United States Patent
Gao et al.

(10) Patent No.: US 9,874,506 B2
(45) Date of Patent: Jan. 23, 2018

(54) DOWNHOLE SYSTEMS FOR DETECTING A PROPERTY OF A FLUID

(71) Applicant: Halliburton Energy Services, Inc., Houston, TX (US)

(72) Inventors: Li Gao, Katy, TX (US); Michael T. Pelletier, Houston, TX (US); Dingding Chen, Tomball, TX (US); Nestor Rodriguez, Shenandoah, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 125 days.

(21) Appl. No.: 15/024,316

(22) PCT Filed: Nov. 6, 2013

(86) PCT No.: PCT/US2013/068767
§ 371 (c)(1),
(2) Date: Mar. 23, 2016

(87) PCT Pub. No.: WO2015/069239
PCT Pub. Date: May 14, 2015

(65) Prior Publication Data
US 2016/0216187 A1 Jul. 28, 2016

(51) Int. Cl.
*G01N 11/00* (2006.01)
*H01F 1/44* (2006.01)
(Continued)

(52) U.S. Cl.
CPC .............. *G01N 11/00* (2013.01); *E21B 49/08* (2013.01); *E21B 49/081* (2013.01); *E21B 49/10* (2013.01);
(Continued)

(58) Field of Classification Search
CPC ............ G01N 2011/0073; G01N 11/00; G01N 9/002; G01N 2009/004; E21B 49/10; E21B 2049/085; H01F 1/447
See application file for complete search history.

(56) References Cited

U.S. PATENT DOCUMENTS 6,378,364 B1 * 4/2002 Pelletier .................. E21B 47/06
73/152.47
8,443,875 B2 * 5/2013 Lee ........................ E21B 10/322
166/66.5
(Continued)

FOREIGN PATENT DOCUMENTS

WO 2013109716 A1 7/2013

OTHER PUBLICATIONS

International Search Report and Written Opinion dated Jul. 23, 2014 issued in corresponding application No. PCT/US2013/068767, 5 pgs.

*Primary Examiner* — Justin Olamit
(74) *Attorney, Agent, or Firm* — Chamberlain Hrdlicka

(57) ABSTRACT

System, methods, and apparatuses for determining properties of a production fluid downhole are presented. In one instance, a system includes a sample-filled sensing device for vibrating a first suspended tube containing a sample of production fluid and producing a first response signal. The system also includes a reference-fluid sensing device with a second suspended tube containing a viscosity-tunable fluid therein. The system vibrates the second suspended tube to create a second response signal. The viscosity of the viscosity-tunable fluid is varied until it is deemed to match that of the sample production fluid. Other systems and methods are presented.

20 Claims, 8 Drawing Sheets

(51) Int. Cl.
  *E21B 49/08* (2006.01)
  *E21B 49/10* (2006.01)
  *G01N 9/00* (2006.01)

(52) U.S. Cl.
  CPC ........ *H01F 1/447* (2013.01); *E21B 2049/085* (2013.01); *G01N 2009/004* (2013.01); *G01N 2011/0073* (2013.01)

(56) References Cited

U.S. PATENT DOCUMENTS

| | | | |
|---|---|---|---|
| 9,008,977 B2* | 4/2015 | Gao | G01N 35/00 |
| | | | 702/1 |
| 9,200,512 B2* | 12/2015 | Goodwin | E21B 47/06 |
| 9,568,409 B2* | 2/2017 | Harrison | G01N 11/16 |
| 9,568,410 B2* | 2/2017 | Gao | G01N 11/16 |
| 2003/0166470 A1* | 9/2003 | Fripp | E21B 21/10 |
| | | | 507/100 |
| 2006/0000603 A1 | 1/2006 | Zazovsky et al. | |
| 2009/0025928 A1 | 1/2009 | Lee | |
| 2009/0200046 A1 | 8/2009 | Goodwin et al. | |
| 2012/0055242 A1 | 3/2012 | Tustin et al. | |

\* cited by examiner

US 9,874,506 B2

DOWNHOLE SYSTEMS FOR DETECTING A PROPERTY OF A FLUID

TECHNICAL FIELD

The disclosure relates to oil and gas exploration and production, and more particularly, but not by way of limitation to downhole systems, apparatuses, and methods for detecting at least one property of a fluid.

BACKGROUND

Crude oil and natural gas occur naturally in subterranean deposits and their extraction includes drilling a well. The well provides access to a production fluid that often contains crude oil and natural gas. In the course of drilling or producing a well it is often desirable to know as much as possible about the production fluid.

DETAILED DESCRIPTION OF ILLUSTRATIVE EMBODIMENTS

Figure 1:
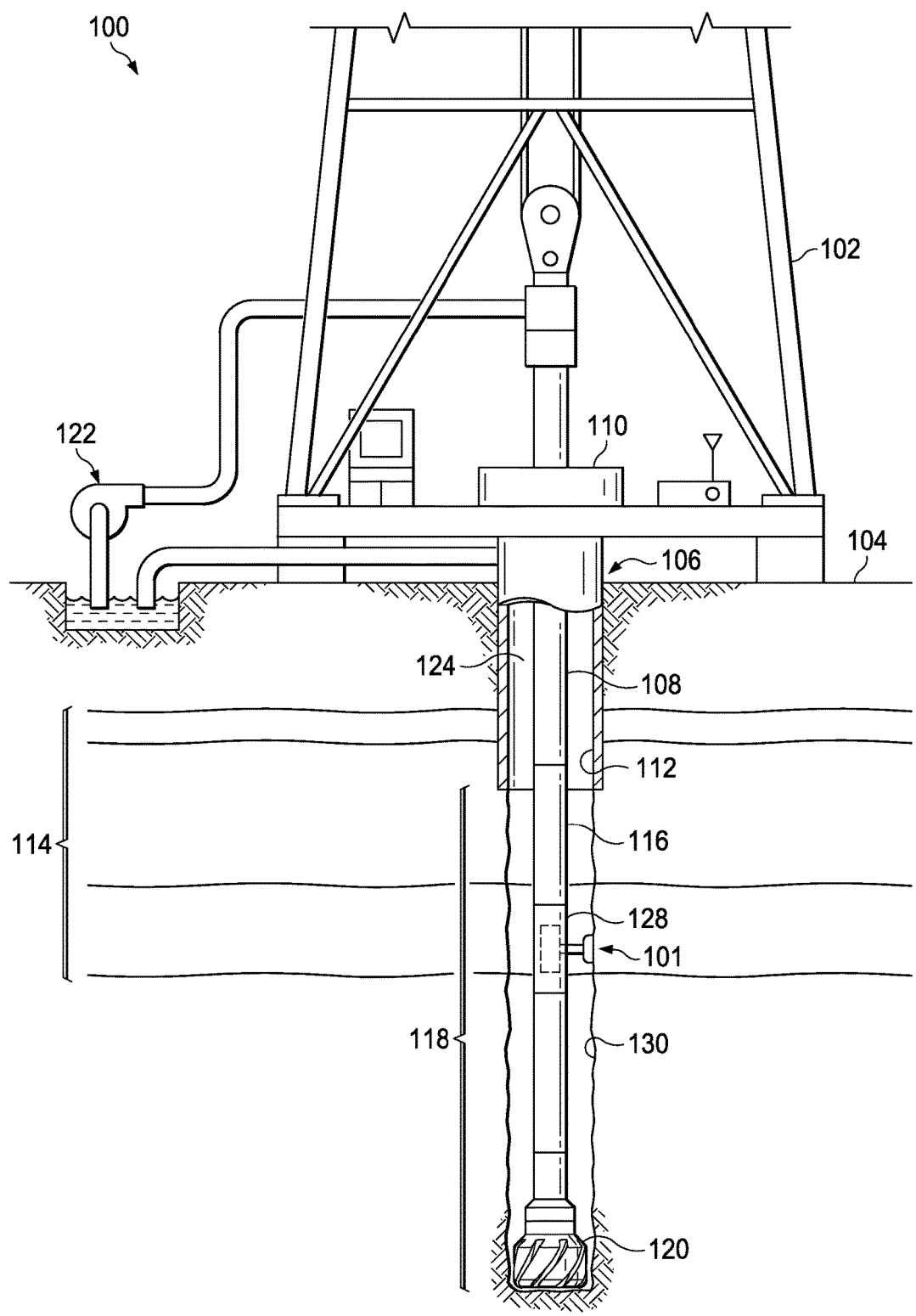
FIG. 1 is a schematic elevation view with a portion shown in cross section of an illustrative embodiment of a well system including a measurement system.

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments is defined only by the appended claims.

In the drawings and description that follow, like parts are typically marked throughout the specification and drawings with the same reference numerals, respectively. The drawing figures are not necessarily to scale. Certain features of the invention may be shown exaggerated in scale or in somewhat schematic form and some details of conventional elements may not be shown in the interest of clarity and conciseness.

The embodiments described herein relate to systems, tools, and methods for determining fluid properties of a production fluid from a wellbore. In one illustrative embodiment, a downhole tool and system are disclosed that determine a viscosity of the production fluid by comparing quality factors of a vibrating tube containing the production fluid to a vibrating tube containing a reference fluid. By utilizing a viscosity-tunable fluid as the reference fluid, the viscosity of the viscosity-tunable fluid may be manipulated until the quality factors are substantially equal, the viscosity of the production fluid then being equivalent to the viscosity of the reference fluid. The downhole tool and system disclosed herein may also determine a density of the production fluid by measuring a resonance frequency of the vibrating tube containing the production fluid and relating the resonance frequency to the density of the production fluid. Other systems, tools and methods are presented.

Unless otherwise specified, any use of any form of the terms "connect," "engage," "couple," "attach," or any other term describing an interaction between elements is not meant to limit the interaction to direct interaction between the elements and may also include indirect interaction between the elements described. In the following discussion and in the claims, the terms "including" and "comprising" are used in an open-ended fashion, and thus should be interpreted to mean "including, but not limited to". Unless otherwise indicated, as used throughout this document, "or" does not require mutual exclusivity.

As used herein, the term "coupled", when used in conjunction with a viscosity-control device and a viscosity-tunable fluid, refers to a magnetic field, an electric field, a combination thereof, or other means to manipulate the rheological state of the viscosity-tunable fluid. In some embodiments, the phrases "magnetic coupling" and "magnetically coupled" describe a magnetic field applied by the viscosity-control device to the viscosity-tunable fluid, the magnetic field operable to align magnetically-active particles suspended in the fluid. In other embodiments, the phrases "electric-field coupling" and "coupled by electric field" describe an electric field applied by the viscosity-control device to the viscosity-tunable fluid. The electric field is operable to align electrically-active particles suspended in the fluid. In other illustrative embodiments, the phrases "electromagnetic coupling" and "electromagnetically coupled" describe a combination of electric and magnetic fields applied by the viscosity-control device to the viscosity-tunable fluid. The combined field is operable to align a combination of electric- and magnetically-active particles suspended in the fluid. The presence of field-active particles in each embodiment enables the viscosity-control device to interact with the viscosity-tunable fluid thereby coupling the two components.

As used herein, the terms "vibration actuator" and "vibration transducer" are intended to include devices that convert energy into motion and motion into energy, respectively. The energy types may include, but are not limited to, mechanical, chemical, electrical, electromagnetic (i.e., light), acoustic, and thermal energies. In some embodiments, the vibration actuator may include a voice coil for converting electrical energy into mechanical vibrations. In other embodiments, the vibration transducer may include a voice coil for converting mechanical vibrations into electrical energy. Other means may be used as well.

The various characteristics mentioned above, as well as other features and characteristics described in more detail below, will be readily apparent to those skilled in the art with the aid of this disclosure upon reading the following detailed description of the embodiments, and by referring to the accompanying drawings. Other means may be used as well.

Referring now primarily to FIG. 1, a well system 100 includes measurement system 101 for determining a fluid property of a production fluid. The system 100 includes a drilling rig 102 located at a surface 104 of a well 106. The drilling rig 102 provides support for a drill string 108 which penetrates a rotary table 110 for drilling a wellbore 112 through subterranean formations 114. The drill string 108 includes a drill pipe 116 coupled to a downhole assembly 118, the downhole assembly 118 terminating in a drill bit 120. A drilling fluid supply subsystem 122 pumps drilling fluid through the interior of the drill string 108 and down to the drill bit 120. An annular gap 124 between the drill string 108 and wellbore 112 enables a return circuit back to the surface 104 where the drilling fluid may be processed. The downhole assembly 118 includes the measurement system 101, or downhole system, for extracting and measuring fluid properties of a production fluid from the wellbore 112. In an embodiment, the downhole system 101 may be attached to a drill collar 128. The attachment allows access to a wellbore wall 130. Additional aspects of the system 101 are presented further below. The measurement system 101 may also be used in a wireline embodiment.

Figure 2:
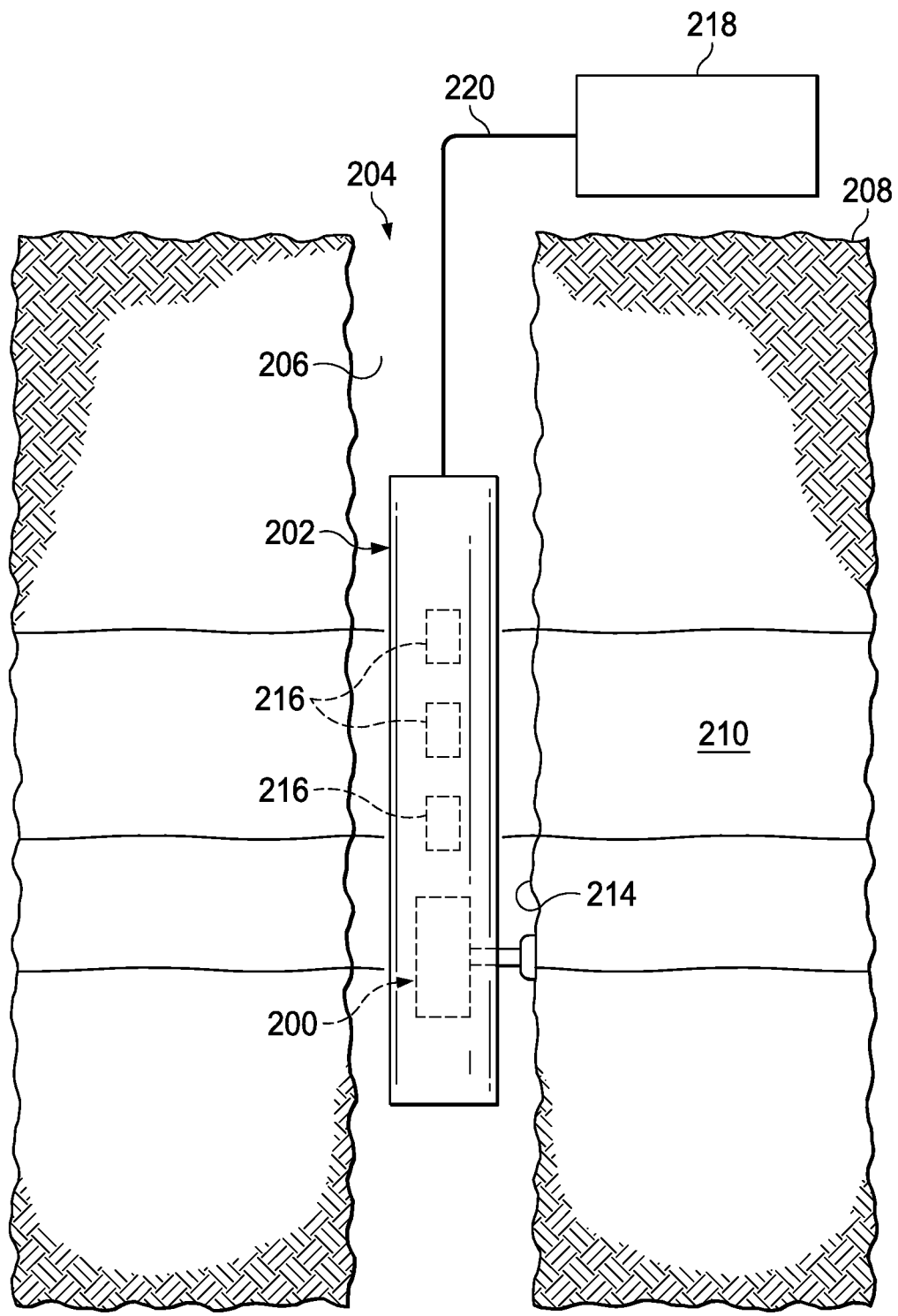
FIG. 2 is a schematic elevation view with a portion shown in cross section of an illustrative embodiment of a wireline system including a measurement system.

For example, referring now primarily to FIG. 2, a measurement system 200, or downhole system, for determining a fluid property of a production fluid is presented in the context of a wireline operation. A logging tool 202 is deployed in a well 204 having a wellbore 206 that extends from a surface 208 of the well 204 to or through subterranean formations 210. The logging tool 202 includes the system 200 for determining a fluid property of a production fluid. The downhole system 200 is coupled to the logging tool 202 and has access to a wellbore wall 214. The logging tool 202 may include one or more instrument packages 216 to monitor and record one or more parameters of the well 204 (e.g., formation densities, neutron porosities, radiation intensities, etc.). The logging tool 202 is connected to a surface unit 218 by a logging cable 220. The logging cable 220 supports the logging tool 202 in the wellbore 206. The logging cable 220 may include a wireline having multiple power and communication lines, a mono-cable having only a single conductor, or a slick-line with no conductors for power or communication.

Figure 3:
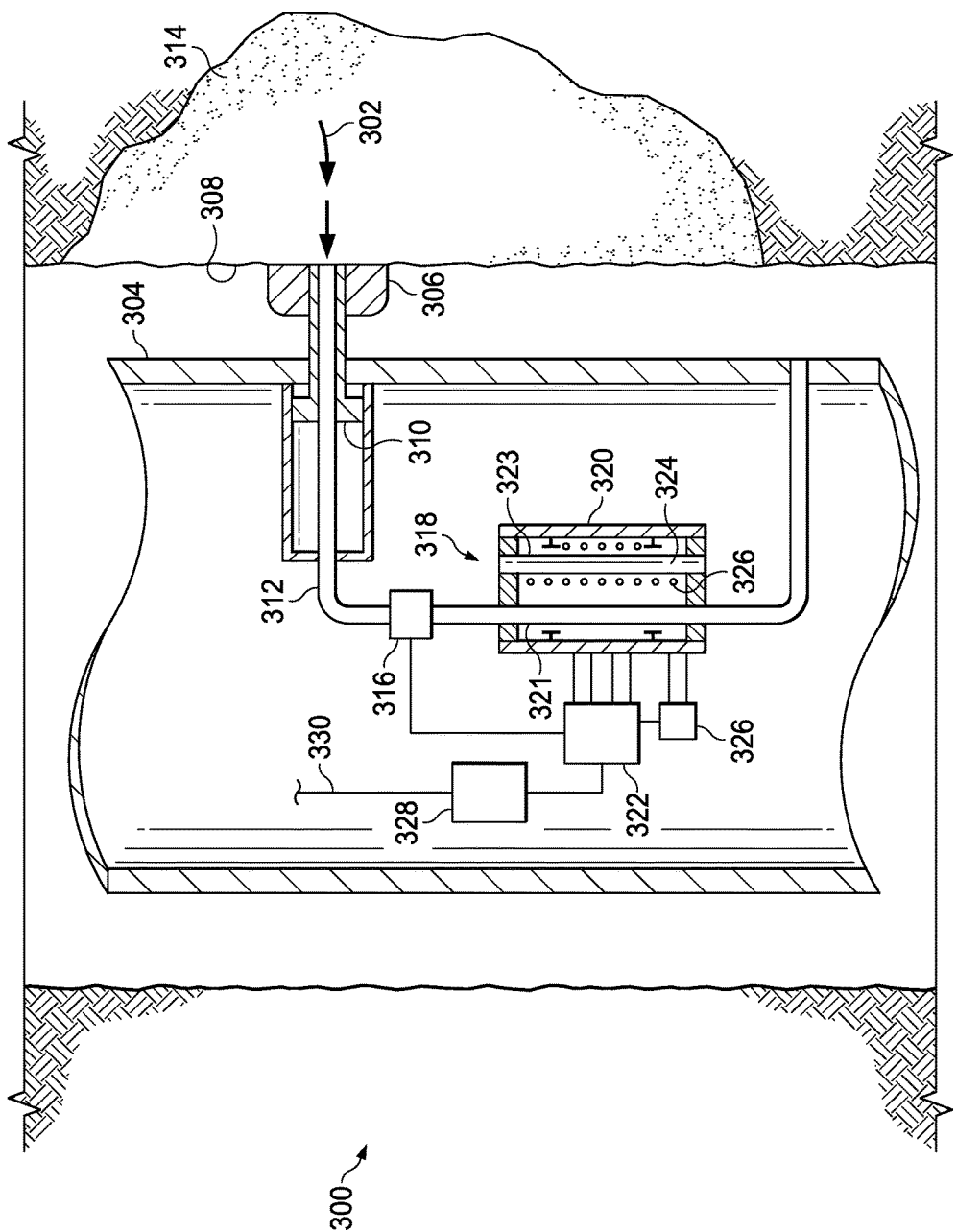
FIG. 3 is a schematic elevation view with a portion shown in cross section of an illustrative embodiment of a measurement system downhole.

Referring now primarily to FIG. 3, an illustrative embodiment of a measurement system 300 for determining a fluid property of a production fluid 302 is presented. The measurement system 300 may be coupled to a body 304, such as that of the drill collar 128 depicted in FIG. 1 or the logging tool 202 depicted in FIG. 2 or another body, and includes a probe 306 for making contact with or being positioned proximate a wellbore wall 308. The probe 306 is coupled to a piston 310, which is operable to extend or retract the probe 306 from the wellbore wall 308. A sample-fluid conduit 312 extends through the probe 306 to enable fluid transfer between subterranean formations 314, which includes the wellbore wall 308, and a pump 316. The suction side of the pump 316 is in fluid communication with the subterranean formations 314 allowing the extraction of production fluid 302 from the subterranean formations 314. The sample-fluid conduit 312 is fluidly coupled to the pressure side of the pump 316 and to an apparatus 318 for determining a fluid property of the production fluid 302. Delivery of the production fluid 302 occurs via the sample-fluid conduit into a measurement unit 320. Delivery of the production fluid 302 is controlled by an analysis unit 322, or controller, coupled to the pump 316.

The analysis unit 322 is further coupled to the measurement unit 320 and processes signals from the measurement unit 320 to determine the fluid properties of the production fluid 302. A viscosity-tunable fluid 324 is disposed within the measurement unit 320 and functions as a reference fluid when viscosity is the property under measurement. The viscosity-tunable fluid 324 is coupled to a viscosity-control device 326 for manipulating the viscosity of the viscosity-tunable fluid 324 in response to signals from the analysis unit 322. The analysis unit 322 is coupled to the viscosity-control device 326 to enable the exchange of such signals. The analysis unit 322 may also be coupled to a communication unit 328 for exchanging data with a surface unit. The transmission of data may occur over a data line 330, a wireless communication channel through mud pulse telemetry, or other technique.

The production fluid 302 is delivered to the measurement unit 320 and is disposed within a sample-fluid sensing device 321. There the production fluid 302 may be compared with the viscosity-tunable fluid 324 disposed within a reference-fluid sensing device 323 as described in more detail elsewhere herein.

Figure 4:
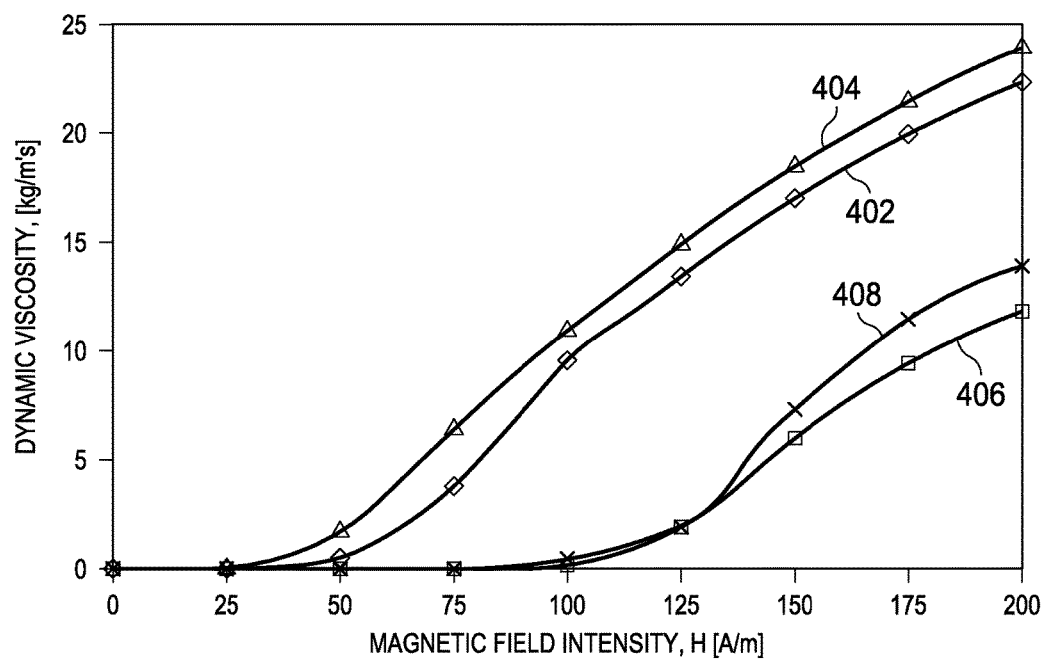
FIG. 4 is a graph showing the viscosity response of four non-limiting, illustrative viscosity-tunable fluids to variations in coupling strength as altered by a viscosity-control device.

Numerous fluids may be used as the viscosity-tunable fluid 324 provided the fluid allows the viscosity to be controlled. Referring now primarily to FIG. 4, an illustrative embodiment of a type of fluid that might be used is presented. FIG. 4 depicts the coupling of a viscosity-tunable fluid to a viscosity-control device. In this embodiment, the viscosity-tunable fluid 324 is a magneto-rheological fluid and the viscosity-control device includes a magnetic-field generator. Four fluid compositions are presented as non-limiting, representative examples of magneto-rheological fluids: a first composition including 20 wt. % carbonyl iron (CI) and fumed silica stabilizer ("Aerosil 200") in silicone oil (OKS 1050) shown by curve 402; a second composition including 40 wt. % carbonyl iron (CI) and fumed silica stabilizer ("Aerosil 200") in silicone oil (OKS 1050) shown by curve 404; a third composition including 20 wt. % carbonyl iron (CI) in silicone oil (OKS 1050) shown by curve 406; and a fourth composition including 40 wt. % carbonyl iron (CI) in silicone oil (OKS 1050) shown by curve 408. In each of the representative examples, the viscosity of the magneto-rheological fluid varies as a function of magnetic field strength. The magnetic field is thus operable to couple the magnetic-field generator to the magneto-rheological fluid.

The four response curves 402, 404, 406, and 408 of FIG. 4 demonstrate a correspondence between a strength of the applied magnetic field and a viscosity of the magneto-rheological fluid. Thus, application of a specific strength by the viscosity-control device 326 (FIG. 3), e.g., magnetic-field generator, permits the selection, in a predictable manner, of a viscosity of a magneto-rheological fluid. Control of the coupling between the magneto-rheological fluid and magnetic-field generator therefore permits the magneto-rheological fluid to function as a viscosity-tunable reference fluid.

In other embodiments, the viscosity-tunable fluid may be an electro-rheological fluid and the viscosity-control device an electric-field generator, wherein the strength of the electric-field coupling is altered to manipulate the viscosity of the electro-rheological fluid. In still further embodiments, the viscosity-tunable fluid may be an electromagneto-rheological fluid and the viscosity-control device an electromagnetic-field generator, wherein the strength of the electromagnetic coupling is altered to manipulate the viscosity of the combined electromagneto-rheological fluid.

Figure 5:
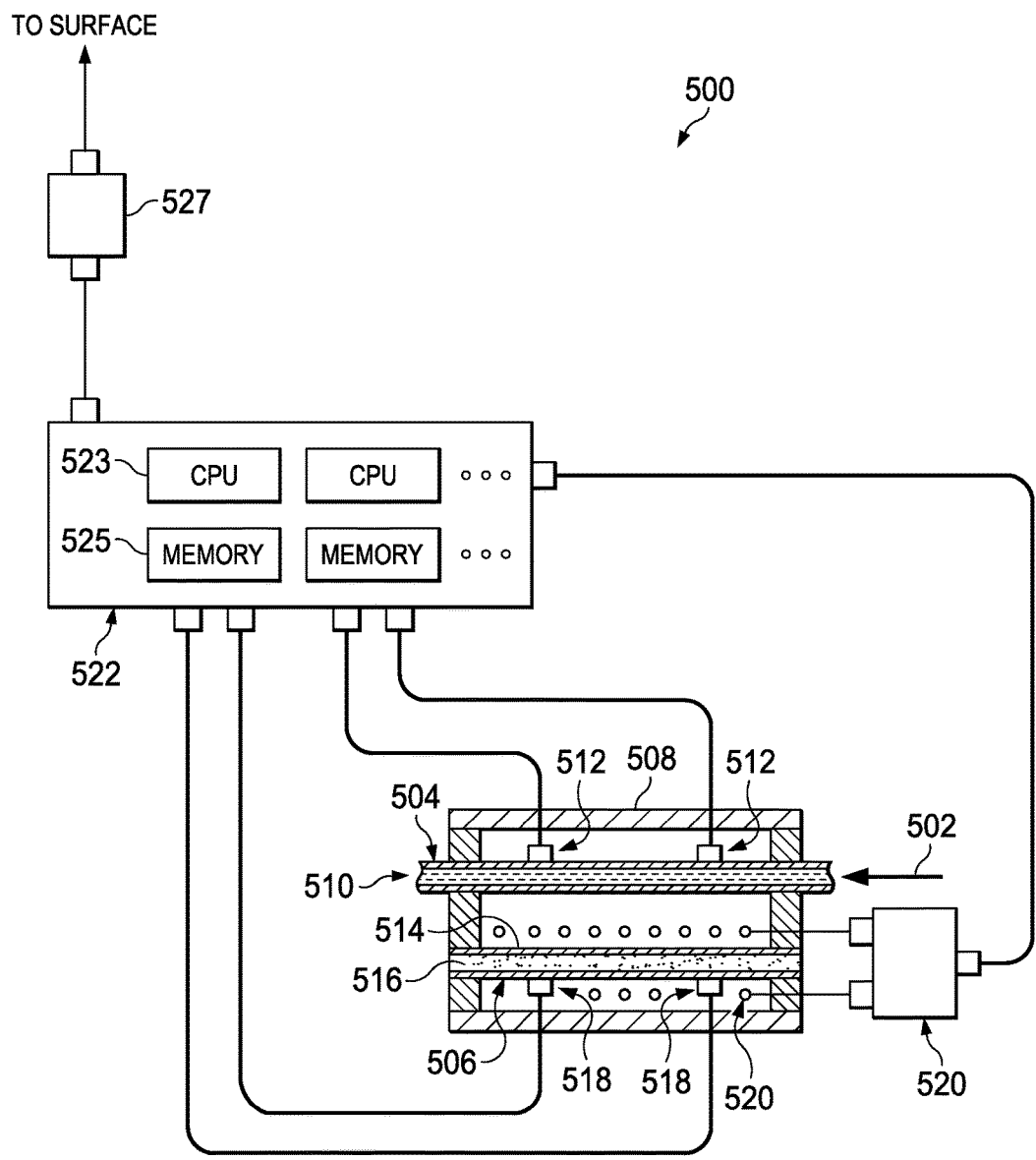
FIG. 5 is a schematic diagram of a measurement system for determining a fluid property of a production fluid in an illustrative embodiment.

Referring now primarily to FIG. 5, an illustrative embodiment of a measurement system or downhole system 500 for determining a fluid property of a production fluid 502 is presented. The system 500 includes a sample-fluid sensing device 504 and a reference-fluid sensing device 506. The sample-fluid sensing device 504 and reference-fluid sensing device 506 may be coupled to a housing 508. The sample-fluid sensing device 504 includes a first suspended tube 510 for receiving and containing a production fluid 502. A first response-signal generator 512 is coupled to the first suspended tube 510. The first response-signal generator 512 is operable to produce a response signal representing a first parameter that is characteristic of the first suspended tube 510 with the production fluid 502 contained therein. The reference-fluid sensing device 506 includes a second suspended tube 514. A viscosity-tunable fluid 516 is disposed within the second suspended tube 514. A second response-signal generator 518 is coupled to the second suspended tube 514. The second response-signal generator 518 is operable to produce a response signal representing a second parameter that is characteristic of the second suspended tube 514 with the viscosity-tunable fluid 516 contained therein.

A viscosity-control device 520 is coupled to the viscosity-tunable fluid 516 to manipulate a viscosity of the viscosity-tunable fluid 516. Coupled to the viscosity-control device 520 is an analysis unit 522, or controller. The analysis unit 522 regulates the coupling between the viscosity-control device 520 and viscosity-tunable fluid 516 in order to select a viscosity of the viscosity-tunable fluid 516. The analysis unit 522 may include look-up tables, parameterized functional expressions, or artificial intelligence (e.g., neural networks, fuzzy logic, etc.) to correlate the strength of the coupling to the viscosity of the viscosity-tunable fluid 516. The analysis unit 522 is also coupled to the first response-signal generator 512 and the second response-signal generator 518. The analysis unit 522 includes one or more processors 523 and one or more memories 525 to carry out various functions, such as providing control signals to and receiving response signals from the generators 512 and 518. The analysis unit 522 processes response signals from the first response-signal generator 512 and second response-signal generator 518 to determine the first and second parameters, respectively. The analysis unit 522 may also be coupled to a communication unit 527 for communicating data to the surface and optionally receiving data or instructions from the surface.

Figure 6:
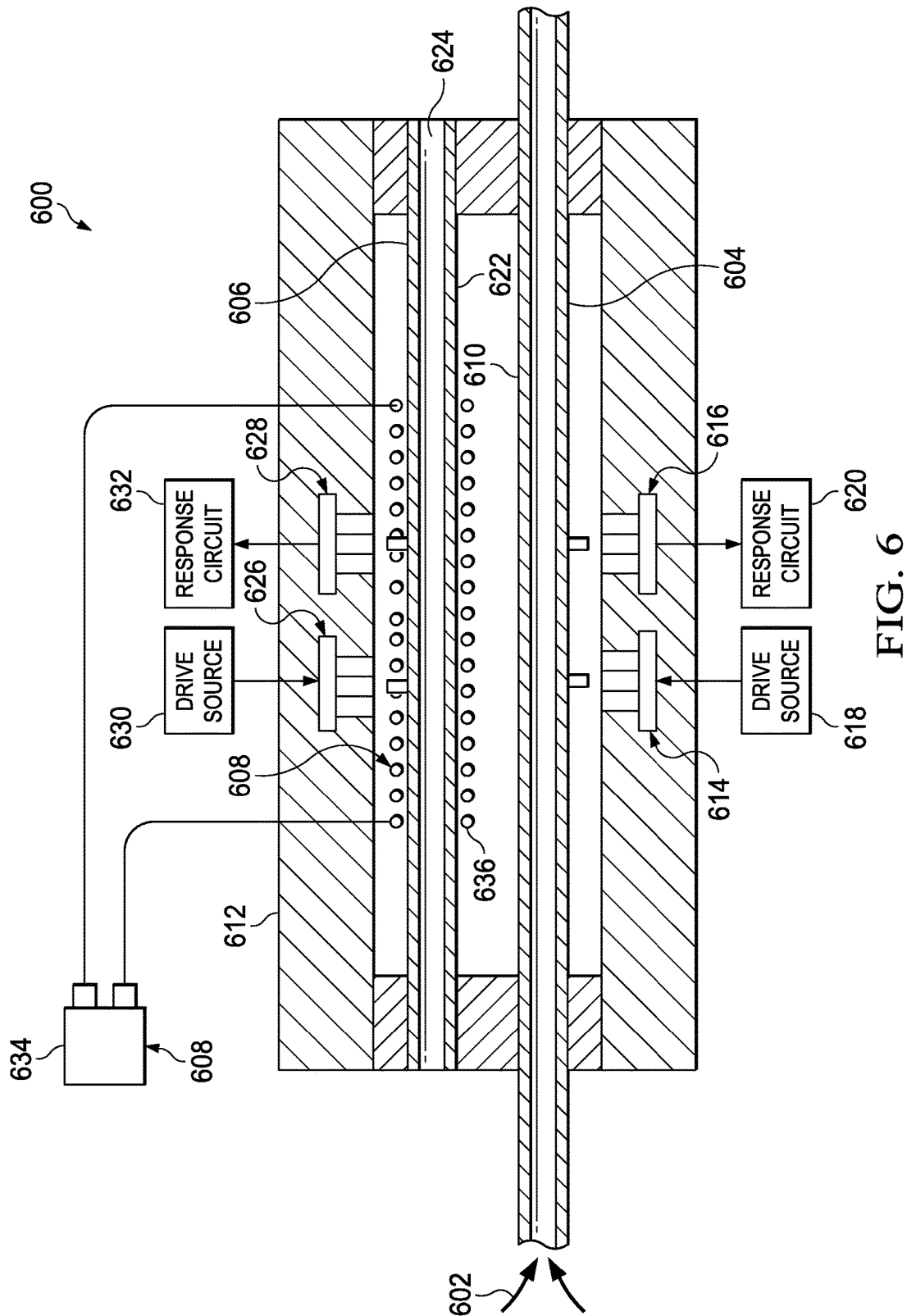
FIG. 6 is a schematic diagram of an apparatus for determining a fluid property of a production fluid in an illustrative embodiment.

Referring now primarily to FIG. 6, one embodiment is presented for an apparatus 600 for determining a fluid property of a fluid sample 602 from a well. The apparatus 600 includes a sample-fluid sensing device 604, and a reference-fluid sensing device 606 coupled to a housing 612. The apparatus 600 also includes a viscosity-control device 608 associated with the sample-fluid sensing device 604.

The sample-fluid sensing device 604 includes a first suspended tube 610 for receiving and containing a fluid sample 602. The first suspended tube 610 may be coupled to the housing 612. The first suspended tube 610 is also coupled to a first vibration actuator 614 and a first vibration transducer 616. The first vibration actuator 614 is operable to induce vibration in the first suspended tube 610. The first vibration transducer 616 is operable to convert vibration energy from the first suspended tube 610 into electrical signals. Electrically coupled to the first vibration actuator 614 may be a first drive source 618. The first drive source 618 provides energy to the first vibration actuator 614 to vibrate the first suspended tube 610. A first response circuit 620 is electrically coupled to the first vibration transducer 616 to generate a first response signal representing the response of the first suspended tube 610 to vibration by the first vibration actuator 614.

The reference-fluid sensing device 606 includes a second suspended tube 622 containing a viscosity-tunable fluid 624. The second suspended tube 622 may be coupled to the housing 612. The second suspended tube 622 is also coupled to a second vibration actuator 626 and a second vibration transducer 628. The second vibration actuator 626 is operable to induce vibration in the second suspended tube 622. The second vibration transducer 628 is operable to convert vibration energy from the second suspended tube 622 into electrical signals. Electrically coupled to the second vibration actuator 626 is a second drive source 630. The second drive source 630 provides energy to the second vibration actuator 626 to vibrate the second suspended tube 622. A second response circuit 632 is electrically-coupled to the second vibration transducer 628 to generate a second response signal representing the response of the second suspended tube 622 to vibration by the second vibration actuator 626. The drive source and response circuit may be wed with a multiplexer in some embodiments. The viscosity-control device 608 is coupled to the viscosity-tunable fluid 624 disposed within the second suspended tube 622. The viscosity-control device 608 is operable to regulate the strength of the coupling to control a viscosity of the viscosity-tunable fluid 624. The viscosity-control device 608 may include a variable power source 634 and a solenoid 636 to produce a magnetic field for coupling to the viscosity-tunable fluid.

In operation, the sample fluid sensing device 604 receives the sample fluid 602 in the first suspended tube 610. The first drive source 618 provides energy to the first vibration actuator 614 in the form of a first drive signal. The first drive signal is operable to cause the first vibration actuator 614 to vibrate the first suspended tube 610 containing the sample fluid 602. Vibrations of the first suspended tube 610, while containing the sample fluid 602, are converted into energy by the first vibration transducer 616. The first response circuit 620 measures energy output from the first vibration transducer 616, producing a first response signal. The first response signal represents a change in signal relative to the first drive signal. The first response signal is generated in response to the first drive signal and the change in signal occurs as the first suspended tube 610 containing the sample fluid 602 is being vibrated.

In similar manner, the second drive source 630 of the reference fluid sensing device 606 provides energy to the second vibration actuator 626 in the form of a second drive signal. The second drive signal is operable to cause the second vibration actuator 626 to vibrate the second suspended tube 622 and the viscosity-tunable fluid 624 therein. Vibrations of the second suspended tube 622, while containing the viscosity-tunable fluid 624, are converted into energy by the second vibration transducer 628. The second response circuit 632 measures energy output from the second vibration transducer 628, producing a second response signal. The second response signal represents a change in signal relative to the second drive signal. The second response signal is generated in response to the second drive signal and the change in signal occurs as the second suspended tube 622 containing the viscosity-tunable fluid 624 is being vibrated.

In an embodiment, the first drive signal and second drive signal may be a sinusoidal signal represented by $y(t)=A \cos(\omega t)$, where A is an amplitude of the sinusoidal signal, $\omega$ is a frequency of the sinusoidal signal, and t is a length of time elapsed since the sinusoidal signal was first applied. Other continuous drive signals may be used. In another embodiment, the first and second drive signal may include an impulse excitation such as that achieved by contacting the first suspended tube and the second suspended tube with a hammer.

In one embodiment, the amplitude of the sinusoidal signal, A, may be modulated by a modulation function, $M(\omega_m)$, having a modulation frequency, $\omega_m$, less than the frequency of the sinusoidal signal, $\omega$. The modulation function may be a square wave function or a sinusoidal function. Other modulation functions are possible. The inclusion of a modulating function serves to partition the drive signal into two drive components. Vibrating tubes may therefore be driven by a drive signal at one frequency (e.g., the sinusoidal frequency, $\omega$), while a response is induced by a drive signal at another frequency (e.g., the modulation frequency, $\omega_m$). Such capability is desirable when measuring attenuations in a vibrating tube. A single-frequency excitation risks stalling the vibrating tube when pausing the drive signal to measure attenuation. A vibrating tube that ceases to vibrate may be difficult to restart, and accordingly one may want to avoid allowing the vibration to stop.

Referring now back to FIG. 6, the first response circuit 620 and second response circuit 632 generate a first response signal and second response signal, respectively, in response to a first drive signal and a second drive signal. The first response signal may be monitored by an analysis unit to produce a first attenuation coefficient. Similarly, the second response signal may be monitored to yield a second attenuation coefficient.

In some embodiments, a response signal represented by $y(t)=Ae^{-\beta t} \cos(\omega t+\varphi)$ is generated in response to a drive signal represented by $y(t)=A \cos(\omega t)$, where the exponential term, $e^{-\beta t}$, corresponds to an attenuation (i.e., change of signal), $\beta$ is an attenuation coefficient characterizing the attenuation, and $\varphi$ corresponds to a phase delay. In other embodiments, a response signal represented by $y(t)=[A \cdot M(\omega_m)]e^{-\beta t} \cos(\omega t)$ is generated in response to a drive signal represented by $y(t)=[A \cdot M(\omega_m)] \cos(\omega t)$, where the exponential term, $e^{-\beta t}$, corresponds to an attenuation (i.e., change of signal), $\beta$ is an attenuation coefficient characterizing the attenuation, and $\varphi$ corresponds to a phase delay.

The attenuation coefficient, $\beta$, is a vibration characteristic used by the analysis unit to determine a quality factor of a vibrating tube. The first attenuation coefficient is therefore used by the analysis unit to determine a first quality factor of the first suspended tube 610 containing the sample fluid 602. Similarly, the second attenuation coefficient is used to determine a second quality factor of the second suspended tube 622 containing the viscosity-tunable fluid 624. With the first quality factor known, the analysis unit works cooperatively with the viscosity-control unit 608 to alter the viscosity of the viscosity-tunable fluid 624 until the second quality factor is substantially equal to the first quality factor. It will be appreciated that the attenuation behavior of the second suspended tube 622 is influenced by the viscosity of the viscosity-tunable fluid 624 contained therein. The second attenuation coefficient, and hence the second quality factor, may therefore be manipulated by altering the viscosity of the viscosity-tunable fluid 624. When the second quality factor is substantially equal to the first quality factor, the analysis unit assigns the viscosity of the viscosity-tunable fluid 624 to the sample fluid 602.

In one embodiment, the analysis unit may also monitor an amplitude of the first response signal. The amplitude of the first response signal may change as a frequency of the first drive signal is varied. Such variation is used to identify a maximum amplitude which correlates to a resonant frequency. The analysis unit relates the resonant frequency to a density of the sample fluid 602 contained in first suspended tube 610. Other parameters and vibration characteristics may be measured by the analysis unit in order to determine other properties of the production fluid as desired.

Figure 7:
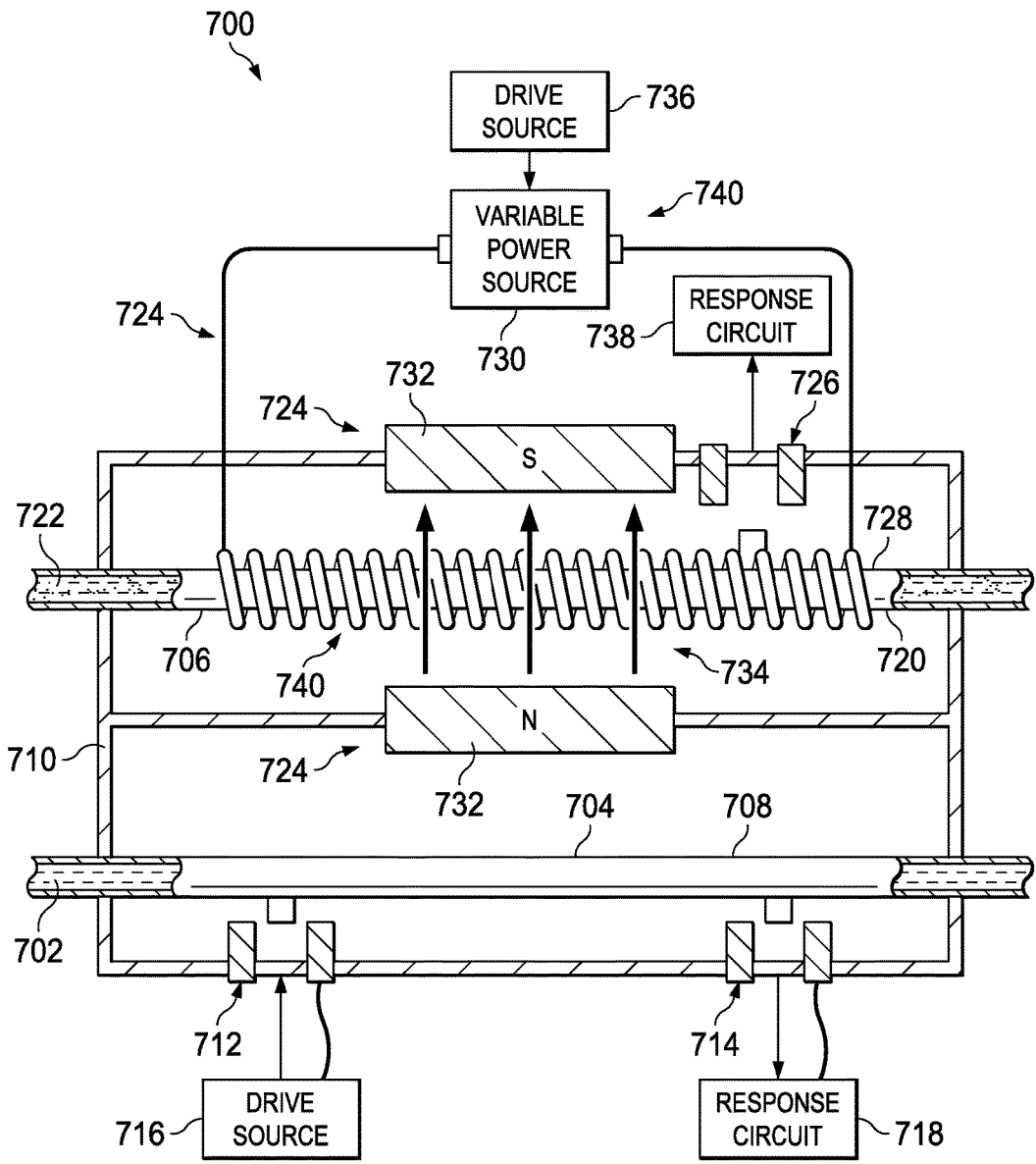
FIG. 7 is a schematic diagram of an apparatus, including a magnetic-field generator, for determining a fluid property of a production fluid in an illustrative embodiment.

FIG. 7 depicts an illustrative embodiment of an apparatus 700 for determining a fluid property of a fluid sample 702 from a well. The apparatus 700 includes a sample-fluid sensing device 704 and a reference-fluid sensing device 706. The sample-fluid sensing device 704 includes a first suspended tube 708 for receiving and containing a fluid sample 702. The first suspended tube 708 is coupled to a housing 710. The first suspended tube 708 is also coupled to a first vibration actuator 712 and a first vibration transducer 714. The first vibration actuator 712 is operable to induce vibration in the first suspended tube 708. The first vibration transducer 714 is operable to convert vibration energy from the first suspended tube 708 into electrical signals. Electrically coupled to the first vibration actuator 712 may be a first drive source 716. The first drive source 716 provides energy to the first vibration actuator 712 to vibrate the first suspended tube 708. A first response circuit 718 is electrically coupled to the first vibration transducer 714 to generate a first response signal representing the response of the first suspended tube 708 to vibration by the first vibration actuator 712.

The reference-fluid sensing device 706 includes a second suspended tube 720. A magneto-rheological fluid 722 is disposed within the second suspended tube 720. The second suspended tube 720 is coupled to the housing 710. The second suspended tube 720 is coupled to a second vibration actuator 724 and a second vibration transducer 726. The second vibration actuator 724 is operable to induce vibration in the second suspended tube 720. The second vibration transducer 726 is operable to convert vibration energy from the second suspended tube 720 into electrical signals. The second vibration actuator 724 includes a solenoid 728 having a longitudinal axis parallel with and typically coincident with a longitudinal axis of the second suspended tube 720. A variable power source 730 is electrically coupled to the solenoid 728, and a magnetic-field generator 732 is proximate to the solenoid 728. The magnetic-field generator 732 provides a unidirectional magnetic field 734 and is positioned such that magnetic field lines emanating from the magnetic-field generator 732 orient substantially perpendicular to the longitudinal axis of the solenoid 728. The magnetic-field generator 732 may include a permanent magnet, a Halbach array of permanent magnets, an electromagnet, or another magnetic source operable to produce a pair of magnetic poles. Electrically coupled to the variable power source 730 is a second drive source 736. Vibration of the second suspended tube 720 is induced when the variable power source 730 is driven by the second drive source 736 to produce an alternating current through the solenoid 728. A second response circuit 738 is electrically coupled to the second vibration transducer 726 to generate a second response signal representing the response of the second suspended tube 720 to vibration by the second vibration actuator 724.

A viscosity-control device 740 is coupled to the magneto-rheological fluid 722 contained in the second suspended tube 720. The viscosity-control device 740 is operable to regulate the strength of the coupling in order to control the viscosity of the magneto-rheological fluid 722. The viscosity-control device 740 may include the variable power source 730 and the solenoid 728 of the second vibration actuator 724. In an embodiment, the variable power source 730 is operated to superimpose a direct-current bias onto the alternating current employed to vibrate the second suspended tube 720. The solenoid 728 responds to the direct-current bias by superimposing a static magnetic-field bias onto the alternating magnetic field used to vibrate the second suspended tube 720. The static magnetic-field bias enables a magnetic-coupling to the magneto-rheological fluid 722. The magnetic coupling allows manipulation of the viscosity of the magneto-rheological fluid 722 by the viscosity-control device 740.

Figure 8:
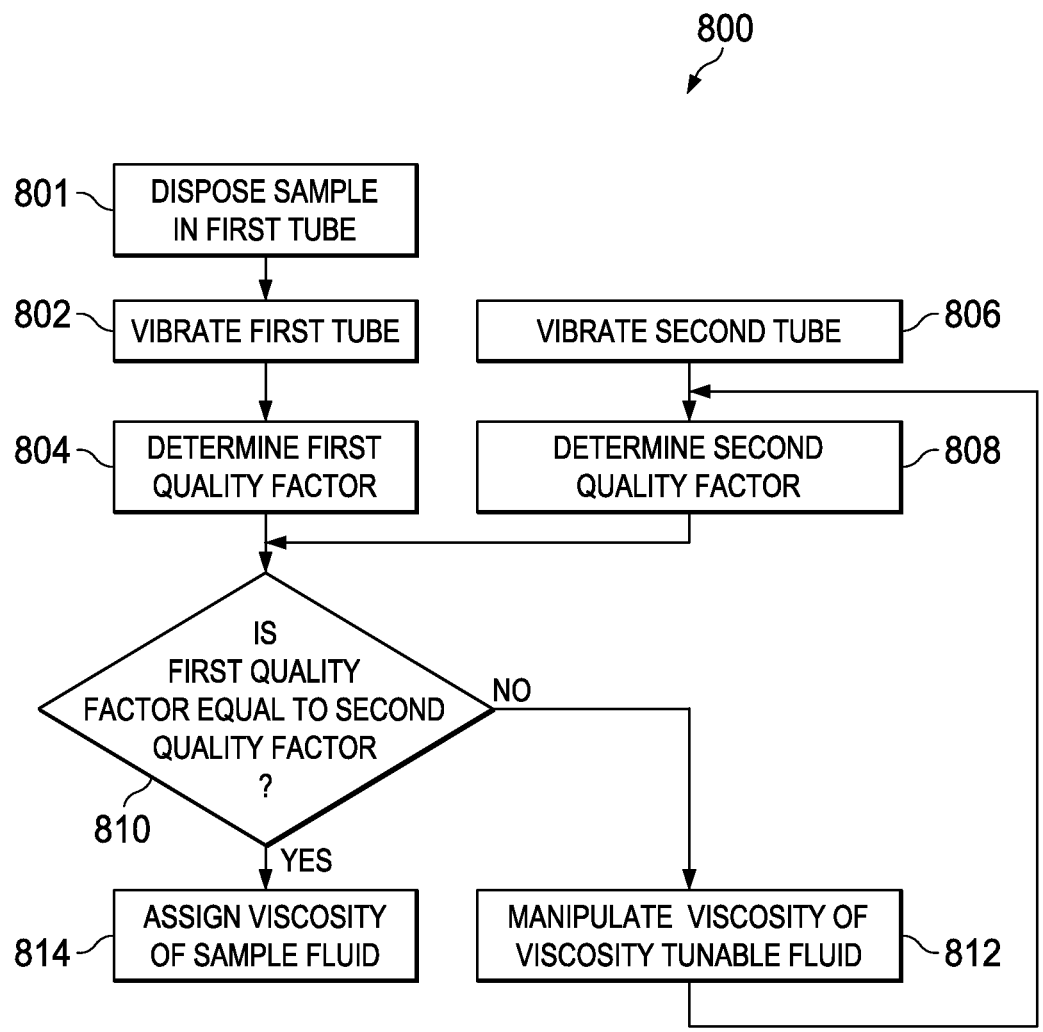
FIG. 8 is a flow chart depicting an illustrative method for determining the viscosity of a production fluid using a viscosity-tunable fluid.

Referring now primarily to FIG. 8, a flow chart shown therein depicts an illustrative method 800 for determining the viscosity of a production fluid in a well according to one embodiment. The method may be used with any of the previous illustrative embodiments. The method includes disposing a sample fluid from the well in a first suspended tube, wherein the sample fluid has a first viscosity (block 801). The method further includes vibrating the first suspended tube (block 802); determining a first vibration characteristic of the first suspended tube including the quality factor (block 804); vibrating a second suspended tube containing a viscosity-tunable fluid (block 806); determining a second vibration characteristic of the second suspended tube including a second quality factor (block 808); comparing the second quality factor to the first (block 810); manipulating a viscosity of the viscosity-tunable fluid until the viscosity of the viscosity-tunable fluid substantially equals the first viscosity of the sample fluid (block 812); and assigning the viscosity of the viscosity-tunable fluid to the sample fluid when the second quality factor substantially equals the first quality factor (block 814). In an illustrative embodiment, the viscosity-tunable fluid includes a magneto-rheological fluid and the viscosity-control device includes a magnetic-field generator. The viscosity of the magneto-rheological fluid is manipulated by altering the strength of the magnetic coupling between the magnetic-field generator and the magneto-rheological fluid.

In another embodiment, the method may further include: determining the resonant frequency of the first suspended tube containing the sample fluid from the well and relating the resonant frequency of the first suspended tube to the density of the production fluid. Other fluid properties may also be determined.

In addition to the illustrative embodiments described above, many examples of specific combinations are within the scope of the disclosure, some of which are presented below.

Example 1

A downhole system for determining a fluid property of a production fluid in a wellbore, the system comprising:
a housing;
a sample-fluid sensing device coupled to the housing, wherein the sample-fluid sensing-device comprises:
a first suspended tube for containing the production fluid, and
first response-signal generator coupled to the first suspended tube for generating a first response signal, the first response signal representing a first parameter that is characteristic of the first suspended tube and the production fluid;
a reference-fluid sensing device coupled to the housing, wherein the reference-fluid sensing device comprises:
a second suspended tube for containing a viscosity-tunable fluid, and
a second response-signal generator coupled to the second suspended tube, the second response-signal generator for generating a second response signal representing a second parameter that is characteristic of the second suspended tube and the viscosity-tunable fluid;
a viscosity-control device coupled to the viscosity-tunable fluid for manipulating a viscosity of the viscosity-tunable fluid; and
an analysis unit coupled to the sample-fluid sensing device, the analysis unit further coupled to the reference-fluid sensing device, and the analysis unit further coupled to the viscosity-control device, the analysis unit comprising one or more processors and one or more memories, and wherein the one or more processors and one or more memories are operable to:
provide a first control signal to the first response-signal generator to control vibration of the first suspended tube,
receive the first response signal and produce a first quality factor,
provide a second control signal to the second response-signal generator to control vibration of the second suspended tube,
receive the second response signal and produce a second quality factor,
provide a viscosity-control signal to the viscosity-control device to manipulate the viscosity of the viscosity-tunable fluid, and
compare the first quality factor and second quality factor and manipulate the viscosity-control signal until the second quality factor substantially equals the first quality factor.

Example 2

The system of example 1, further comprising a communication unit for receiving and communicating fluid data to a surface unit.

Example 3

The system of example 1 or 2, wherein the viscosity-tunable fluid comprises a magneto-rheological fluid, wherein the one or more processors and one more memories derives a first quality factor by producing an attenuation coefficient from the first response signal.

Example 4

The system of example 1 or any of examples 2-3, wherein the one or more processors and one more memories is operable to provide a first control signal to the first response-signal generator to vibrate the first suspended tube until a resonance frequency is established and identifying a density of the sample fluid based on the resonance frequency.

Example 5

The system of example 1 or any of examples 2-4, wherein the viscosity-control device comprises a solenoid electrically coupled to a variable power source, wherein the variable power source is operable to vary a strength of a magnetic field produced by the solenoid, and wherein the viscosity of the magneto-rheological fluid varies as a function of the strength of the magnetic field.

Example 6

The system of example 1 or any of examples 2-4, wherein the reference-fluid sensing device further comprises:
  a solenoid having a longitudinal axis coincident with a longitudinal axis of the second suspended tube;
  a variable power source coupled to the solenoid, the variable power source operable to produce an alternating current and a direct-current bias in the solenoid; and
  a magnetic-field generator providing a unidirectional magnetic field, the magnetic-field generator positioned such that magnetic field lines emanating from the magnetic field generator orient substantially perpendicular to the longitudinal axis of the solenoid.

Example 7

The system of example 1 or example 2 or 4,
  wherein the viscosity-tunable fluid comprises a magneto-rheological fluid;
  wherein the one or more processors and one more memories produces a first quality factor by producing an attenuation coefficient from the first response signal;
  wherein the reference-fluid sensing device further comprises:
    a solenoid having a longitudinal axis coincident with a longitudinal axis of the second suspended tube,
    a variable power source coupled to the solenoid, the variable power source operable to produce an alternating current and a direct-current bias in the solenoid, and
    a magnetic-field generator providing a unidirectional magnetic field, the magnetic-field generator positioned such that magnetic field lines emanating from the magnetic field generator orient substantially perpendicular to the longitudinal axis of the solenoid; and
  wherein the viscosity-control device comprises the solenoid and variable power source, wherein the direct-current bias of the variable power source is operable to vary the non-alternating strength of the magnetic field produced by the solenoid, and wherein the viscosity of the magneto-rheological fluid varies as a function of the non-alternating strength of the magnetic field.

Example 8

An apparatus for determining a fluid property of a sample fluid from a well comprising:
  a sample-fluid sensing device comprising:
    a first suspended tube for receiving a sample fluid,
    a first vibration actuator coupled to the first suspended tube,
    a first vibration transducer coupled to the first suspended tube,
    a first drive source electrically coupled to the first vibration actuator for providing energy to the first vibration actuator to vibrate the first suspended tube, and
    a first response circuit electrically coupled to the first vibration transducer for generating a first response signal representing a response of the first suspended tube to vibration by the first vibration actuator;
  a reference-fluid sensing device comprising:
    a second suspended tube containing a viscosity-tunable fluid,
    a second vibration actuator coupled to the second suspended tube,
    a second vibration transducer coupled to the second suspended tube,
    a second drive source electrically coupled to the second vibration actuator for providing energy to the second vibration actuator to vibrate the second suspended tube,
    a second response circuit electrically coupled to the second vibration transducer for generating a second response signal representing a second response of the second suspended tube to vibration by second actuator; and
  a viscosity-control device coupled to the viscosity-tunable fluid, the viscosity-control device operable to regulate the strength of the coupling to control a viscosity of the viscosity-tunable fluid.

Example 9

The apparatus of example 8, further comprising a housing, and wherein the sample-fluid sensing device and reference-fluid sensing device are coupled to the housing.

Example 10

The apparatus of example 8 or example 9, wherein the viscosity-tunable fluid comprises a magneto-rheological fluid and the viscosity-controllable device comprises a magnetic-field generator magnetically coupled to the magneto-rheological fluid.

Example 11

The apparatus of example 8 or any of examples 9-10, wherein the magneto-rheological fluid comprises carbonyl iron in suspension.

Example 12

The apparatus of example 8 or any of examples 9-11, wherein the a magnetic-field generator comprises a solenoid electrically coupled to a variable power source, and wherein the variable power source is operable to vary the strength of a magnetic field produced by the solenoid.

Example 13

The apparatus of example 8 or any of examples 9-11, wherein the second vibration actuator comprises:
  a solenoid having a longitudinal axis coincident with a longitudinal axis of the second suspended tube;

a variable power source electrically coupled to the solenoid, the variable power source operable to produce an alternating current and direct-current bias in the solenoid; and a magnetic-field generator proximate to the solenoid, wherein the magnetic-field generator provides a unidirectional magnetic field, wherein the magnetic-field generator is positioned such that magnetic field lines emanating from the magnetic-field generator orient substantially perpendicular to the longitudinal axis of the solenoid.

Example 14

The apparatus of example 13, wherein the viscosity-control device comprises the solenoid and the variable power source of the second vibration actuator.

Example 15

A method for determining the viscosity of a production fluid in a well, the method comprising:
disposing a sample fluid from the well in a first suspended tube, wherein the sample fluid has a first viscosity;
vibrating the first suspended tube;
determining a first vibration characteristic of the first suspended tube;
vibrating a second suspended tube containing a viscosity-tunable fluid;
determining a second vibration characteristic of the second suspended tube;
manipulating a viscosity of the viscosity-tunable fluid until the viscosity of the viscosity-tunable fluid substantially equals the first viscosity of the sample fluid.

Example 16

The method of example 15, wherein manipulating a viscosity of the viscosity-tunable fluid comprises altering the strength of a coupling between a viscosity-control device and the viscosity-tunable fluid.

Example 17

The method of example 15 or 16, wherein the coupling comprises a magnetic field and wherein the viscosity-tunable fluid comprises a magneto-rheological fluid.

Example 18

The method of example 15 or any of examples 16-17 wherein the first vibration characteristic comprises a first quality factor of the first suspended tube and the second vibration characteristic comprises a second quality factor of the second suspended tube.

Example 19

The method of example 15 or any of examples 16-17 or 19,
wherein the second vibration characteristic comprises a second quality factor of the second suspended tube
wherein determining the second quality factor of the second suspended tube comprises:
measuring a change in a second response signal sensed from the second suspended tube, the change in the second response signal relative to a second drive signal applied to vibrate the second suspended tube, the second response signal generated in response to the second drive signal such that the change in second response signal occurs as the second suspended tube is being vibrated.
monitoring an attenuation in the measured change to determine a second attenuation coefficient; and
deriving the second quality factor from the second attenuation coefficient.

Example 20

The method of example 15 or any of examples 16-19, further comprising:
determining a resonant frequency of the first suspended tube containing the sample fluid from the well; and
relating the resonant frequency of the first suspended tube to the density of the production fluid.

Example 21

A system for determining a fluid property of a production fluid in a wellbore, the system comprising:
a sample-fluid sensing device, wherein the sample-fluid sensing-device comprises:
a first suspended tube for containing the production fluid, and
first response-signal generator coupled to the first suspended tube for generating a first response signal, the first response signal representing a first parameter that is characteristic of the first suspended tube and the production fluid;
a reference-fluid sensing device, wherein the reference-fluid sensing device comprises:
a second suspended tube for containing a viscosity-tunable fluid, and
a second response-signal generator coupled to the second suspended tube, the second response-signal generator for generating a second response signal representing a second parameter that is characteristic of the second suspended tube and the viscosity-tunable fluid;
a viscosity-control device coupled to the viscosity-tunable fluid for manipulating a viscosity of the viscosity-tunable fluid; and
an analysis unit coupled to the sample-fluid sensing device, the analysis unit further coupled to the reference-fluid sensing device, and the analysis unit further coupled to the viscosity-control device, the analysis unit comprising one or more processors and one or more memories, and wherein the one or more processors and one or more memories are operable to:
provide a first control signal to the first response-signal generator to control vibration of the first suspended tube,
receive the first response signal and produce a first quality factor,
provide a second control signal to the second response-signal generator to control vibration of the second suspended tube,
receive the second response signal and produce a second quality factor,
provide a viscosity-control signal to the viscosity-control device to manipulate the viscosity of the viscosity-tunable fluid, and compare the first quality factor and second quality factor and manipulate the viscosity-control signal until the second quality factor substantially equals the first quality factor.

Example 22

An apparatus for determining a fluid property of a sample fluid comprising:
a sample-fluid sensing device comprising:
  a first suspended tube for receiving a sample fluid,
  a first vibration actuator coupled to the first suspended tube,
  a first vibration transducer coupled to the first suspended tube,
  a first drive source electrically coupled to the first vibration actuator for providing energy to the first vibration actuator to vibrate the first suspended tube, and
  a first response circuit electrically coupled to the first vibration transducer for generating a first response signal representing a response of the first suspended tube to vibration by the first vibration actuator;
a reference-fluid sensing device comprising:
  a second suspended tube containing a viscosity-tunable fluid,
  a second vibration actuator coupled to the second suspended tube,
  a second vibration transducer coupled to the second suspended tube,
  a second drive source electrically coupled to the second vibration actuator for providing energy to the second vibration actuator to vibrate the second suspended tube,
  a second response circuit electrically coupled to the second vibration transducer for generating a second response signal representing a second response of the second suspended tube to vibration by second actuator; and
a viscosity-control device coupled to the viscosity-tunable fluid, the viscosity-control device operable to regulate the strength of the coupling to control a viscosity of the viscosity-tunable fluid.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in connection to any one embodiment may also be applicable to any other embodiment.

It will be understood that the benefits and advantages described above may relate to one embodiment or may relate to several embodiments. It will further be understood that reference to "an" item refers to one or more of those items.

The steps of the methods described herein may be carried out in any suitable order or simultaneous where appropriate. Where appropriate, aspects of any of the examples described above may be combined with aspects of any of the other examples described to form further examples having comparable or different properties and addressing the same or different problems.

In some embodiments, the first vibration actuator and first vibration transducer may comprise, respectively, the second vibration actuator and the second vibration transducer. In other embodiments, the first suspended tube may comprise the second suspended tube. In such embodiments, a plumbing sub-system may serve to alternate the contents of the second suspended tube between the fluid sample and the viscosity-tunable fluid.

It will be understood that the above description of preferred embodiments is given by way of example only and that various modifications may be made by those skilled in the art. The above specification, examples, and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:
1. A downhole system for determining a fluid property of a production fluid in a wellbore, the system comprising:
  a housing;
  a sample-fluid sensing device coupled to the housing, wherein the sample-fluid sensing-device comprises:
    a first suspended tube for containing the production fluid, and
    first response-signal generator coupled to the first suspended tube for generating a first response signal, the first response signal representing a first parameter that is characteristic of the first suspended tube and the production fluid;
  a reference-fluid sensing device coupled to the housing, wherein the reference-fluid sensing device comprises:
    a second suspended tube for containing a viscosity-tunable fluid, and
    a second response-signal generator coupled to the second suspended tube, the second response-signal generator for generating a second response signal representing a second parameter that is characteristic of the second suspended tube and the viscosity-tunable fluid;
  a viscosity-control device coupled to the viscosity-tunable fluid for manipulating a viscosity of the viscosity-tunable fluid; and
  an analysis unit coupled to the sample-fluid sensing device, the analysis unit further coupled to the reference-fluid sensing device, and the analysis unit further coupled to the viscosity-control device, the analysis unit comprising one or more processors and one or more memories, and wherein the one or more processors and one or more memories are operable to:
    provide a first control signal to the first response-signal generator to control vibration of the first suspended tube,
    receive the first response signal and produce a first quality factor,
    provide a second control signal to the second response-signal generator to control vibration of the second suspended tube,
    receive the second response signal and produce a second quality factor,
    provide a viscosity-control signal to the viscosity-control device to manipulate the viscosity of the viscosity-tunable fluid, and
    compare the first quality factor and second quality factor and manipulate the viscosity-control signal until the second quality factor substantially equals the first quality factor.

2. The system of claim 1, further comprising a communication unit for receiving and communicating fluid data to a surface unit.

3. The system of claim 1, wherein the viscosity-tunable fluid comprises a magneto-rheological fluid, wherein the one or more processors and one more memories derives a first quality factor by producing an attenuation coefficient from the first response signal.

4. The system of claim 1, wherein the one or more processors and one more memories is operable to provide a first control signal to the first response-signal generator to vibrate the first suspended tube until a resonance frequency is established and identify a density of the sample fluid based on the resonance frequency.

5. The system of claim 1, wherein the viscosity-control device comprises a solenoid electrically coupled to a variable power source, wherein the variable power source is operable to vary a strength of a magnetic field produced by the solenoid, and wherein the viscosity of the magneto-rheological fluid varies as a function of the strength of the magnetic field.

6. The system of claim 1, wherein the reference-fluid sensing device further comprises:
a solenoid having a longitudinal axis coincident with a longitudinal axis of the second suspended tube;
a variable power source coupled to the solenoid, the variable power source operable to produce an alternating current and a direct-current bias in the solenoid; and
a magnetic-field generator providing a unidirectional magnetic field, the magnetic-field generator positioned such that magnetic field lines emanating from the magnetic field generator orient substantially perpendicular to the longitudinal axis of the solenoid.

7. The system of claim 1,
wherein the viscosity-tunable fluid comprises a magneto-rheological fluid;
wherein the one or more processors and one more memories produces a first quality factor by producing an attenuation coefficient from the first response signal;
wherein the reference-fluid sensing device further comprises:
a solenoid having a longitudinal axis coincident with a longitudinal axis of the second suspended tube,
a variable power source coupled to the solenoid, the variable power source operable to produce an alternating current and a direct-current bias in the solenoid, and
a magnetic-field generator providing a unidirectional magnetic field, the magnetic-field generator positioned such that magnetic field lines emanating from the magnetic field generator orient substantially perpendicular to the longitudinal axis of the solenoid; and
wherein the viscosity-control device comprises the solenoid and variable power source, wherein the direct-current bias of the variable power source is operable to vary a non-alternating strength of the magnetic field produced by the solenoid, and wherein the viscosity of the magneto-rheological fluid varies as a function of the non-alternating strength of the magnetic field.

8. An apparatus for determining a fluid property of a sample fluid from a well comprising:
a sample-fluid sensing device comprising:
a first suspended tube for receiving a sample fluid, a first vibration actuator coupled to the first suspended tube,
a first vibration transducer coupled to the first suspended tube,
a first drive source electrically coupled to the first vibration actuator for providing energy to the first vibration actuator to vibrate the first suspended tube, and
a first response circuit electrically coupled to the first vibration transducer for generating a first response signal representing a response of the first suspended tube to vibration by the first vibration actuator;
a reference-fluid sensing device comprising:
a second suspended tube containing a viscosity-tunable fluid,
a second vibration actuator coupled to the second suspended tube,
a second vibration transducer coupled to the second suspended tube,
a second drive source electrically coupled to the second vibration actuator for providing energy to the second vibration actuator to vibrate the second suspended tube, a second response circuit electrically coupled to the second vibration transducer for generating a second response signal representing a second response of the second suspended tube to vibration by second actuator; and
a viscosity-control device coupled to the viscosity-tunable fluid, the viscosity-control device operable to control a viscosity of the viscosity-tunable fluid.

9. The apparatus of claim 8, further comprising a housing, and wherein the sample-fluid sensing device and reference-fluid sensing device are coupled to the housing.

10. The apparatus of claim 8, wherein the viscosity-tunable fluid comprises a magneto-rheological fluid and the viscosity-control device comprises a magnetic-field generator magnetically coupled to the magneto-rheological fluid.

11. The apparatus of claim 8, wherein the magneto-rheological fluid comprises carbonyl iron in suspension.

12. The apparatus of claim 8, wherein a magnetic-field generator comprises a solenoid electrically coupled to a variable power source, and wherein the variable power source is operable to vary a strength of a magnetic field produced by the solenoid.

13. The apparatus of claim 8, wherein the second vibration actuator comprises:
a solenoid having a longitudinal axis coincident with a longitudinal axis of the second suspended tube;
a variable power source electrically coupled to the solenoid, the variable power source operable to produce an alternating current and direct-current bias in the solenoid; and
a magnetic-field generator proximate to the solenoid, wherein the magnetic-field generator provides a unidirectional magnetic field, wherein the magnetic-field generator is positioned such that magnetic field lines emanating from the magnetic-field generator orient substantially perpendicular to the longitudinal axis of the solenoid.

14. The apparatus of claim 13, wherein the viscosity-control device comprises the solenoid and the variable power source of the second vibration actuator.

15. A method for determining the viscosity of a production fluid in a well, the method comprising:
disposing a sample fluid from the well in a first suspended tube, wherein the sample fluid has a first viscosity;
vibrating the first suspended tube;
determining a first vibration characteristic of the first suspended tube;

vibrating a second suspended tube containing a viscosity-tunable fluid;
determining a second vibration characteristic of the second suspended tube;
manipulating a viscosity of the viscosity-tunable fluid until the viscosity of the viscosity-tunable fluid substantially equals the first viscosity of the sample fluid.

16. The method of claim 15, wherein manipulating a viscosity of the viscosity-tunable fluid comprises altering a strength of a coupling between a viscosity-control device and the viscosity-tunable fluid.

17. The method of claim 15, wherein a coupling comprises a magnetic field and wherein the viscosity-tunable fluid comprises a magneto-rheological fluid.

18. The method of claim 15 wherein the first vibration characteristic comprises a first quality factor of the first suspended tube and the second vibration characteristic comprises a second quality factor of the second suspended tube.

19. The method of claim 15,
wherein the second vibration characteristic comprises a second quality factor of the second suspended tube, and
wherein determining the second quality factor of the second suspended tube comprises:
measuring a change in a second response signal sensed from the second suspended tube, the change in the second response signal relative to a second drive signal applied to vibrate the second suspended tube, the second response signal generated in response to the second drive signal such that the change in second response signal occurs as the second suspended tube is being vibrated;
monitoring an attenuation in the measured change to determine a second attenuation coefficient; and
deriving the second quality factor from the second attenuation coefficient.

20. The method of claim 15, further comprising:
determining a resonant frequency of the first suspended tube containing the sample fluid from the well; and
relating the resonant frequency of the first suspended tube to the density of the production fluid.

* * * * *